US 11,013,688 B1

United States Patent
Rawert et al.

(10) Patent No.: US 11,013,688 B1
(45) Date of Patent: May 25, 2021

(54) METHODS OF TREATMENT OF VIRAL DISEASES

(71) Applicant: Softhale NV, Diepenbeek (BE)

(72) Inventors: Jürgen Rawert, Cologne (DE); Jan Torsten Tews, Munich (DE)

(73) Assignee: SOFTHALE NV, Diepenbeek (BE)

( * ) Notice: Subject to any disclaimer, the term of this patent is extended or adjusted under 35 U.S.C. 154(b) by 0 days.

(21) Appl. No.: 16/930,340

(22) Filed: Jul. 16, 2020

Related U.S. Application Data

(60) Provisional application No. 63/030,972, filed on May 28, 2020, provisional application No. 63/051,908, filed on Jul. 15, 2020.

(51) Int. Cl.
| | |
|---|---|
| *A61K 9/08* | (2006.01) |
| *A61K 9/12* | (2006.01) |
| *A61K 9/00* | (2006.01) |
| *A61K 31/706* | (2006.01) |

(52) U.S. Cl.
CPC .............. *A61K 9/0078* (2013.01); *A61K 9/08* (2013.01); *A61K 31/706* (2013.01)

(58) Field of Classification Search
CPC ...... A61K 9/0078; A61K 9/08; A61K 31/706; A61K 9/12
See application file for complete search history.

(56) References Cited

U.S. PATENT DOCUMENTS

| | | |
|---|---|---|
| 7,544,712 B1 | 6/2009 | Hsu et al. |
| 2004/0068222 A1 | 4/2004 | Brian |
| 2005/0039738 A1 | 2/2005 | Zimlich et al. |
| 2009/0216183 A1 | 8/2009 | Minotti |
| 2012/0090603 A1 | 4/2012 | Dunne et al. |
| 2012/0298694 A1 | 11/2012 | Holzmann |
| 2014/0076308 A1 | 3/2014 | Dunne |
| 2017/0100551 A1 | 4/2017 | Kendra |

FOREIGN PATENT DOCUMENTS

| | | |
|---|---|---|
| EP | 0925799 A2 | 6/1999 |
| EP | 0627230 B1 | 2/2000 |
| EP | 1792660 A1 | 6/2007 |
| WO | 9114468 A1 | 10/1991 |
| WO | 03103760 A1 | 12/2003 |

(Continued)

OTHER PUBLICATIONS

Common Human Coronaviruses; Treatment for common human coronaviruses [online] retrieved on Aug. 28, 2020 from: https://www.cdc.gov/coronavirus/downloads/Common-HCoV-fact-sheet-508.pdf; 1 page). (Year: 2020).*

(Continued)

*Primary Examiner* — Ernst V Arnold
(74) *Attorney, Agent, or Firm* — Pharma Patents International AG; Lily Ackerman

(57) ABSTRACT

The present invention provides for a method for the treatment of a viral disease, disorder or condition in a subject, the method comprising the step of administering to said subject a medically active liquid in nebulized form by inhalation, wherein the medically active liquid comprises remdesivir or a pharmaceutically acceptable salt thereof and wherein the medically active liquid is administered in nebulized form using an inhalation device.

20 Claims, 4 Drawing Sheets

(56) References Cited

FOREIGN PATENT DOCUMENTS

WO  2018197730 A1  11/2018

OTHER PUBLICATIONS

Spector (J Allergy Clin Immunol 1995;95(5) p. 2: pp. 1133-1137) (Year: 1995).*
Nili et al. ( Rev Med Virol. 2020;e2133:13 pages) (Year: 2020).*
Bryan-Murrago et al. (Medicina Universitaria 2015; 17(68): 165-174)) (Year: 2015).*
Sun, D. (The AAPS Journal; 2020, published online May 26; 22:77; 6 pages). (Year: 2020).*
Written Opinion of the International Application No. PCT/EP2018/061056, dated Nov. 1, 2018, 14 pages.
Chandel, Akshay , et al., "Recent advances in aerosolised drug delivery", Elsevier Masson SAS, Biomedicine & Pharmacotherapy 112 (2019) 108601, 2019, 11 pages.
Hickey, Anthony J., et al., "Pharmaceutical inhalation aerosol technology", Third edition, Boca Raton, CRC Press Taylor & Francis Group, Identifiers: 2018044344, 2019, Section VI.
Ibrahim, Mariam , et al., "Inhalation drug delivery devices: technology update", Dovepress—Medical Devices: Evidence and Research, Feb. 12, 2015, pp. 131-139.
Lo, Michael K., et al., "GS-5734 and its parent nucleoside analog inhibit Filo-, Pneumo-, and Paramyxoviruses", Scientific Reports, vol. 7, DOI: 10.1038/srep43395, 2017, pp. 1-7.
Sheahan, Timothy P., et al., "Broad-spectrum antiviral GS-5734 inhibits both epidemic and zoonotic coronaviruses", Sci. Transl. Med., vol. 9, eaal3653, 2017, pp. 1-10.
Sheahan, Timothy P., et al., "Comparative therapeutic efficacy of remdesivir and combination lopinavir, ritonavir, and interferon beta against MERS-CoV", Nature Communications, vol. 11, No. 222, 2020, pp. 1-14.
Wang, Manli , et al., "Remdesivir and chloroquine effectively inhibit the recently emerged novel coronavirus (2019-nCoV) in vitro", Cell Research, vol. 30, https://doi.org/10.1038/s41422-020-0282-0, 2020, pp. 269-271.
Warren, Travis K., et al., "Therapeutic efficacy of the small molecule GS-5734 against Ebola virus in rhesus monkeys", Nature, vol. 531, 2016, pp. 381-385.

* cited by examiner

FIG. 8

METHODS OF TREATMENT OF VIRAL DISEASES

CROSS REFERENCE TO RELATED APPLICATIONS

This application claims priority to and the benefit of U.S. Provisional Application Ser. No. 63/030,972, filed on May 28, 2020, and U.S. Provisional Application Ser. No. 63/051,908, filed on Jul. 15, 2020, all of which are incorporated herein by reference in their entireties.

BACKGROUND OF THE INVENTION

The present invention relates to the field of methods for the treatment of a viral infection or viral disease, disorder or condition in a subject, by administering to the subject a medically active liquid in nebulized form by inhalation, wherein the medically active liquid comprises remdesivir or a pharmaceutically acceptable salt thereof, and wherein the medically active liquid is administered in nebulized form using an inhalation device. More specifically, the present invention relates to the treatment of a viral infection such as a coronavirus infection or a viral disease, disorder or condition, such as a respiratory or pulmonary disease, disorder or condition, induced by or resulting from a coronavirus infection.

Nebulizers or other aerosol generators for liquids are known in the art. Amongst others, such devices are used in medical science and therapy. There, they serve as inhalation devices for the application of active ingredients in the form of aerosols, i.e., small liquid droplets embedded in a gas. Such an inhalation device is known, e.g., from document EP 0 627 230 B1. Essential components of this inhalation device are a reservoir in which the liquid that is to be aerosolized is contained; a pumping device for generation of a pressure being sufficiently high for nebulizing; as well as an atomizing device in the form of a nozzle. By means of the pumping device, the liquid is drawn in a discrete amount, i.e., not continuously, from the reservoir, and fed to the nozzle. The pumping device works without propellant and generates pressure mechanically.

Remdesivir is an antiviral drug that was authorized by the FDA in May 2020 for emergency use for the treatment of suspected or laboratory confirmed coronavirus disease COVID-19 in adults and child hospitalized with severe disease. Remdesivir has been shown to have anti-viral effects against a novel coronavirus first detected in 2019 named SARS-CoV-2 (a.k.a. 2019-nCoV) which caused the outbreak of the COVID-19 disease. See, e.g., Wang, M. et al., *Cell Research*, Vol. 30, 269-271 (2020, doi:10.1038/s41422-020-0282-0). In addition to COVID-19, remdesivir has been investigated for the treatment of other viral infections. For example, remdesivir has been shown to have anti-viral effects against various viral infections including severe acute respiratory syndrome coronavirus (SARS-CoV), Middle East respiratory syndrome coronavirus (MERS-CoV), Ebola virus (EBOV), Marburg virus, respiratory syncytial virus (RSV), Nipah virus (NiV), and Hendra virus. See, e.g., Warren, T. K. et al., *Nature*, Vol. 531, 381-385 (2016); Lo, M. K et al, *Sci. Rep.*, Vol. 7, 43395 (2017); Sheahan. T. P. et al., *Sci. Transl. Med.*, Vol. 9, eaal3653 (2017); and Sheahan, T. P. et al., *Nature Communications*, Vol. 11, 222 (2020, doi: 10.1038/s41467-019-13940-6). U.S. Pat. No. 7,544,712 discloses methods of treating a coronavirus infection including severe acute respiratory syndrome and porcine transmissible gastroenteritis virus infections by oral, nasal, or parental administration of a variety of compounds. Despite these efforts, soluble, liquid formulations of remdesivir have not been developed for treating viral infections or viral diseases or conditions, such as respiratory diseases or conditions, for pulmonary delivery by inhalation. Such formulations would advantageously deliver the drug to the patient via the highly permeable and large surface area of the lungs in a non-invasive manner with more accurate dosages.

It is thus an object of the present invention to provide a method for the treatment of a viral infection or viral disease, disorder or condition in a subject, especially in an accurate, effective, and patient friendly manner. Further objects of the invention will be clear on the basis of the following description of the invention, examples and claims.

SUMMARY OF THE INVENTION

In a first aspect, the invention relates to a method for the treatment of a viral infection or viral disease, disorder or condition in a subject, the method comprising the step of administering to said subject a medically active liquid in nebulized form by inhalation, wherein the medically active liquid comprises remdesivir or a pharmaceutically acceptable salt thereof, and wherein the medically active liquid is administered in nebulized form using an inhalation device. In some embodiments, the viral disease, disorder or condition is a respiratory or pulmonary disease, disorder or condition.

In a second aspect, the present invention provides for a medically active liquid comprising remdesivir or a pharmaceutically acceptable salt thereof for use in the treatment of a viral infection or viral disease, disorder or condition in a subject, wherein the medically active liquid is administered in nebulized form to said subject using an inhalation device. In some embodiments, the viral disease, disorder or condition is a respiratory or pulmonary disease, disorder or condition.

In a third aspect, the present invention provides for the use of remdesivir or a pharmaceutically acceptable salt thereof for the preparation of a medically active liquid for the treatment of a viral disease, disorder or condition in a subject, wherein the medically active liquid is administered to a subject in nebulized form by inhalation using an inhalation device. In some embodiments, the viral disease, disorder or condition is a respiratory or pulmonary disease, disorder or condition.

In a fourth aspect, the present invention provides for the use of an inhalation device for the treatment of a viral infection or viral disease, disorder or condition in a subject, wherein the medically active liquid is administered in nebulized form using the inhalation device and wherein the medically active liquid comprises remdesivir or a pharmaceutically acceptable salt thereof. In some embodiments, the viral disease, disorder or condition is a respiratory or pulmonary disease, disorder or condition.

BRIEF DESCRIPTION OF THE DRAWINGS

FIG. 8 shows the average particle size distribution results for Example 2.

DETAILED DESCRIPTION OF THE INVENTION

Figure 1:
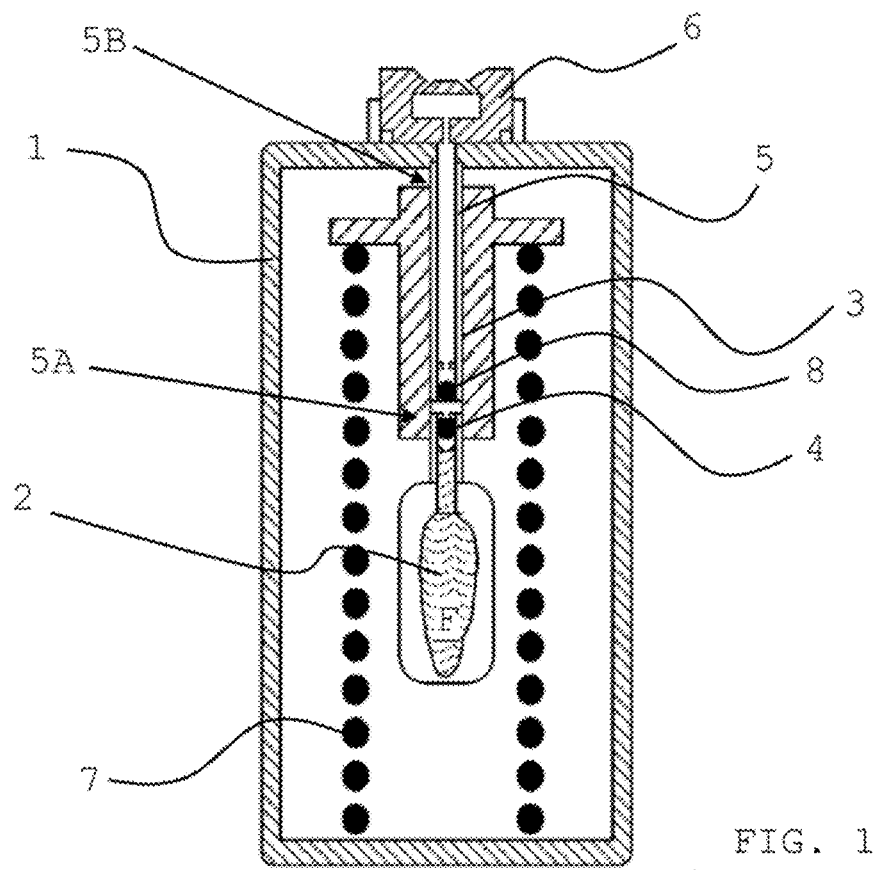
FIG. 1 shows an embodiment of an inhalation device that may be used in the method of the present invention prior to its first use.

In a first aspect, the present invention provides for a method for the treatment of a viral infection or viral disease, disorder or condition in a subject, the method comprising the step of administering to said subject a medically active liquid in nebulized form by inhalation, wherein the medically active liquid comprises remdesivir or a pharmaceutically acceptable salt thereof and wherein the medically active liquid is administered in nebulized form using an inhalation device. In some embodiments, the viral disease, disorder or condition is a respiratory or pulmonary disease, disorder or condition.

The term 'treatment' as used herein, means administration of the compound or composition to a subject to at least ameliorate, reduce or suppress existing signs or symptoms of the infection, disease, disorder or condition experienced by the subject.

The term 'prevention' as used herein means prophylactically administering the formulation to a subject who does not exhibit signs or symptoms of an infection, disease, disorder or condition, but who is expected or anticipated to likely exhibit such signs or symptoms in the absence of prevention. Preventative treatment may at least lessen or partly ameliorate expected symptoms or signs.

The term 'effective amount' as used herein refers to the administration of an amount of the relevant compound or composition sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc.

The terms 'subject' or 'individual' or 'patient' as used herein may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject, individual or patient is a human.

As used herein, the term 'medically active' refers to a compound which has pharmacological activity which improves symptoms associated with a viral infection or viral disease, disorder or condition, such a respiratory disease, disorder or condition.

As used herein, the term 'remdesivir' refers to a compound also known as GS-5734 with the Chemical Abstracts Service (CAS) number [1809249-37-3]. Remdesivir has a molecular weight of 602.6 g/mol and the following structure:

The term 'remdesivir' also includes any pharmaceutically acceptable salt of remdesivir.

The present invention provides for a method for the treatment or prevention of a viral infection or viral disease, disorder or condition in a subject. In some specific aspects, the disease, disorder or condition is associated to, caused by or mediated through a viral infection such as a coronavirus, or specifically the disease COVID-19 caused by severe acute respiratory syndrome coronavirus (SARS-CoV-2). In some embodiments, the viral disease, disorder or condition is a respiratory or pulmonary disease, disorder or condition.

In general terms, a viral disease, disorder or condition may be induced by or result from a viral infection and may be a disease, disorder or condition of the immune system, the cardiovascular system, the endocrine system, the gastrointestinal tract, the renal system, the respiratory system, the central nervous system, or may be a cancer or other malignancy that is caused by or associated with a viral pathogen.

More specifically, a viral disease, disorder or condition as referred to herein may be induced by or result from a viral infection and may be a disease, disorder or condition of the immune system, an inflammatory disease, disorder or condition or an autoimmune disease, disorder or condition, a disease, disorder or condition of the cardiovascular system, a cancer, tumor or other malignancy, a disease, disorder or condition of the renal system, a disease, disorder or condition of the gastro-intestinal tract, a disease, disorder or condition of the respiratory system, a disease disorder or condition of the endocrine system and/or a disease, disorder or condition of the central nervous system (CNS).

According to these specific embodiments, the method according to the present invention allows for the treatment of a viral infection in a patient or subject. Such viral infections may be selected from a broad variety of viral infections including coronaviruses, influenza viruses such as H1N1 influenza or Avian Flu H5N1, rhinoviruses such as human rhinoviruses (HRVs), adenoviruses such as human adenoviruses (HAdV), severe acute respiratory syndrome viruses (SARS) such as severe acute respiratory syndrome coronaviruses (SARS-CoV or SARS-CoV-2), Middle East respiratory syndrome viruses such as Middle East respiratory syndrome coronaviruses (MERS-CoV), Zika viruses (ZIKV), Japanese encephalitis viruses QEV), hepatitis C viruses (HCV), Ebola viruses (EBOV), Chikungunya viruses (CHIKV), Epstein-Barr viruses (EBV), Marburg viruses, respiratory syncytial viruses (RSV), Nipah viruses (NiV), Hendra viruses, and Human Immunodeficiency viruses (HIV). In some embodiments, the viral infection include severe acute respiratory syndrome viruses (SARS)

such as severe acute respiratory syndrome coronaviruses (SARS-CoV or SARS-CoV-2), Middle East respiratory syndrome coronaviruses (MERS-CoV), Ebola viruses (EBOV), Marburg viruses, respiratory syncytial viruses (RSV), Nipah viruses (NiV), and Hendra viruses. In specific embodiments, however, the viral infection to be prevented or treated by the method of the present invention is an infection by a coronavirus. In some embodiments, the viral infection is a pulmonary infection such as a lower respiratory tract infection (e.g., a pneumonia).

In further specific embodiments, the viral infection to be treated or prevented by the method according to the present invention is a SARS-CoV or SARS-CoV-2 virus infection. A SARS-CoV-2 viral infection is believed to be the cause of the pandemic disease COVID-19. Accordingly, in specific embodiments, the method according to the present invention allows for the treatment of viral infections and/or the diseases, disorders or conditions associated with or caused by such viral infection in a subject or patient diagnosed with COVID-19.

In further specific embodiments as mentioned above, the disease, disorder or condition to be treated or prevented according to the present invention is a lower respiratory tract infection, affecting at least a part of the lower respiratory tract of a subject, specifically a human, such as one or both lungs of a subject or patient (e.g., a pneumonia). According to these embodiments, the respiratory disease, disorder or condition may be a pulmonary disease, disorder or condition, whereas the term 'pulmonary' means that such disease affects or is associated with one or both lungs of a subject or patient. In some embodiments, the respiratory disease, disorder or condition or viral disease, disorder or condition may be induced by or result from a viral infection.

Specifically, the viral disease, disorder or condition to be treated or prevented according to the present invention is a severe acute respiratory syndrome (SARS), more specifically a SARS-CoV-2 viral infection. In other specific embodiments, the viral disease, disorder or condition to be treated or prevented according to the present invention is a Middle East respiratory syndrome (MERS), more specifically a Middle East respiratory syndrome coronavirus viral infection.

In specific embodiments, as outlined above, the subject to be treated by the method according to the present invention preferably is a human or warm-blooded animal, especially a human. In some embodiments, the subject is diagnosed with a viral infection, such as a coronavirus infection, especially by a SARS or MERS coronavirus. In further specific embodiments, the subject is diagnosed with COVID-19.

In further specific embodiments, the viral disease, disorder or condition to be treated or prevented by the method of the present invention may be a disease, disorder or condition that results or is caused by an initial infection with a viral pathogen. Such viral diseases, disorders or conditions comprise but are not limited to inflammations or informational processes caused by such an infection such as pneumonia caused by an infection with a coronavirus such as ARS-CoV or SARS-CoV-2.

The method according to the present invention comprises the step of administering a medically active liquid in nebulized form by inhalation to a subject, wherein the medically active liquid comprises remdesivir or a pharmaceutically acceptable salt thereof and wherein the medically active liquid is administered in nebulized form using an inhalation device.

In specific embodiments, the anti-viral effective substance to be administered and comprised by the medically active liquid according to the present invention is remdesivir or a pharmaceutically acceptable salt thereof. Without being bound by any theory, in further embodiments, the remdesivir or a pharmaceutically acceptable salt thereof to be administered and comprised by the medically active liquid may inhibit SARS-CoV or SARS-CoV-2 replication.

In some embodiments, remdesivir is administered as a pharmaceutically acceptable salt. In other embodiments, remdesivir is administered as a solvate. In some specific embodiments, the solvate may comprise one or more solvent molecules, such as, for example, one or more water or alcohol molecules.

In some embodiments, the remdesivir or a pharmaceutically acceptable salt thereof can be used as such as the medically active liquid to be administered in nebulized form according to the present invention. In an alternative embodiments, however, the medically active liquid or, in other words, liquid pharmaceutical composition to be administered by the method according to the invention and comprising remdesivir or a pharmaceutically acceptable salt thereof is preferably formulated as a composition that is suitable, and adapted for inhalative use, in other words a composition that may be nebulized or atomized for inhalation and that is physiologically acceptable for inhalation by a subject, specifically by a human.

The medically active liquid or pharmaceutical composition to be administered by inhalation according to the invention may be in the form of a dispersion, for example a suspension with a liquid continuous phase, and a solid dispersed phase or in the form of a solution. In some embodiments, the medically active liquid or pharmaceutical composition is in the form of a solution where remdesivir is substantially dissolved in the solution. In some embodiments, a solution or solid dispersion of remdesivir is administered to a subject by inhalation to treat a viral infection or viral disease, disorder or condition, such as a respiratory or pulmonary disease, disorder or condition.

In some embodiments, remdesivir is handled as a lyophilisate or lyophilised solid to be reconstituted with a solvent to produce the medically active liquid to be administer to the subject.

In some embodiments, the medically active liquid may comprise a solvent or, in other words, a liquid vehicle as the solvent or continuous phase. In some embodiments, a suitable solvent or liquid vehicle may be an aqueous solvent, a non-aqueous solvent, or mixtures of an aqueous solvent and a non-aqueous solvent. In some preferred embodiments, the solvent is a non-aqueous solvent. In certain specific embodiments, physiologically acceptable solvents comprise but are not limited to alcohols, specifically alcohols with 2 to 4, or preferably 2 or 3, carbon atoms, such as ethanol, propanol or iso-propanol or glycols such as ethylene glycol, propylene glycol, glycerol, lipophilic liquids such as semi-fluorinated alkanes. In some preferred embodiments, the medically active liquid comprises 100% of an alcohol. In some embodiments, the medically active liquid comprises 100% ethanol. In some embodiments, the medically active liquid comprises 100% of a glycol. In other embodiments, the medically active liquid comprises mixtures of one or more alcohols. In yet other embodiments, the medically active liquid comprises mixtures of one or more alcohols and one or more glycols. In yet other embodiments, the medically active liquid comprises mixtures of one or more alcohols and water. In yet other embodiments, the medically active liquid comprises mixtures of one or more glycols and water.

In yet other embodiments, the medically active liquid comprises mixtures of one or more alcohols, one or more glycols, and water.

In some embodiments, the solvent system or liquid vehicle of the medically active liquid may comprise an alcohol as described above, especially ethanol, propanol, iso-propanol, ethylene glycol, or propylene glycol as the only or dominating solvent, e.g., 100 wt.-% of the alcohol. In these cases also, water may be present as a co-solvent, for example, ethanolic solvent system comprising water, e.g., in an amount of up to about 30 wt.-%, or of up to about 20 wt.-%, or of up to about 10 wt.-% or lower, or in other cases ethylene glycol or propylene glycol comprising water, such as of up to about 30 wt.-%, or of up to about 20 wt.-%, or of up to about 10 wt-% or lower.

In some embodiments, the remdesivir or pharmaceutically acceptable salt is dispensed in an amount of about 1 µL, 2 µL, 5 µL, 10 µL, or 15 µL, or at least about 20 µL, 25 µL, 30 µL, or 50 µL. In some embodiments, the remdesivir or pharmaceutically acceptable salt is dispensed in an amount of about 1.5 µL. In some embodiments, the concentration of remdesivir or pharmaceutically acceptable salt in the medically active liquid is about 0.10 µg/µL, 0.25 µg/µL, 0.5 µg/µL, 1 µg/µL, 2 µg/µL, 3 µg/µL, 4 µg/µL, 5 µg/µL, 6 µg/µL, 7 µg/µL, 8 µg/µL, 9 µg/µL, 10 µg/µL, 11 µg/µL, 12 µg/µL, 13 µg/µL, 14 µg/µL, 15 µg/µL, 16 µg/µL, 17 µg/µL, 18 µg/µL, 19 µg/µL, 20 µg/µL, 21 µg/µL, 22 µg/µL, 23 µg/µL, 24 µg/µL, 25 µg/µL, 26 µg/µL, 27 µg/µL, 28 µg/µL, 29 µg/µL, or 30 µg/µL. In some embodiments, the concentration of remdesivir or pharmaceutically acceptable salt in the medically active liquid is about 15 µg/µL, 16 µg/µL, or 17 µg/µL. In other embodiments, the concentration of remdesivir or pharmaceutically acceptable salt in the medically active liquid is about 16 µg/µL. In yet other embodiments, the concentration of remdesivir or pharmaceutically acceptable salt in the medically active liquid is about 15 µg/µL. In some embodiments, the concentration of remdesivir or pharmaceutically acceptable salt in the medically active liquid is about 1 µg/µL to about 10 µg/µL or about 10 µg/µL to about 30 µg/µL.

In some embodiments, the remdesivir or pharmaceutically acceptable salt is dispensed in an amount of about 100 µg to about 300 µg per activation. In other embodiments, the remdesivir or pharmaceutically acceptable salt is dispensed in an amount of about 150 µg to about 300 µg per activation. In other embodiments, the remdesivir or pharmaceutically acceptable salt is dispensed in an amount of about 150 µg to about 230 µg per activation. In other embodiments, the remdesivir or pharmaceutically acceptable salt is dispensed in an amount of about 210 µg to about 250 µg per activation. In other embodiments, the remdesivir or pharmaceutically acceptable salt is dispensed in an amount of about 220 µg to about 230 µg per activation. In other embodiments, the remdesivir or pharmaceutically acceptable salt is dispensed in an amount of about 225 µg per activation.

In further embodiments, the medically active liquid or liquid pharmaceutical composition may comprise, optionally, one or more physiologically acceptable excipients, which are suitable for inhalative use. Excipients which may be used in the medically active liquid or liquid composition include, but are not limited to, one or more buffering agents to regulate or control pH of the solution, chelating agents, salts such as sodium chloride, taste-masking agents, surfactants, lipids, antioxidants, co-solvents, and solubilizing agents, all of which may be used to enhance or improve solubility. In some embodiments, the solubilizing agent is a cyclic oligosaccharide, such as a cyclodextrin. In specific embodiments, the solubilizing agent is cyclodextrin.

Suitable excipients are known to the skilled person and are described, e.g. in standard pharmacopoeias such as U.S.P. or Ph. Eur., or in the Handbook of Pharmaceutical Excipients, 6th ed. Rowe et al, Eds.; The Pharmaceutical Press and the American Pharmaceutical Association: 2009.

Exemplary compounds suitable as buffers for the adjustment of the pH of the present pharmaceutical compositions after reconstitution comprise, for example, sodium dihydrogen phosphate dihydrate and/or disodium hydrogen phosphate dodecahydrate, sodium hydroxide solution, basic salts of sodium, calcium or magnesium such as, for example, citrates, phosphates, acetates, tartrates, lactates etc., amino acids, acidic salts such as hydrogen phosphates or dihydrogen phosphates, especially those of sodium, moreover, organic and inorganic acids such as, for example, hydrochloric acid, sulphuric acid, phosphoric acid, citric acid, cromoglycinic acid, acetic acid, lactic acid, tartaric acid, succinic acid, fumaric acid, lysine, methionine, acidic hydrogen phosphates of sodium or potassium, etc., and further buffer systems as described above. In further specific embodiments, the medically active liquid to be nebulized and administered according to the present invention may comprise one or more further excipients which are selected from chelating agents, for example, disodium edetate dihydrate, calcium sodium EDTA, preferably disodium edetate dihydrate.

Further excipients that may be included in the medically active liquid comprising remdesivir or a pharmaceutically acceptable salt thereof to be administered according to the present invention comprise, but are not limited to phosphatidylcholines, such as dilauroylphosphatidylcholine (DLPC), dipalmitoylphosphatidylcholine (DPPC), distearoylphosphatidyl glycerol (DTPA), diethylene triamine pentaacetic acid, hydrogenated soy phosphatidylcholine (HSPC), multilamellar vesicles, and soy phosphatidylcholine (SPC) such as Tween 80.

The medically active liquid comprising remdesivir or a pharmaceutically acceptable salt thereof to be administered to a subject in need thereof by inhalation may, in further embodiments, additionally comprise at least one further medically active compound or active pharmaceutical ingredient (API).

The amount of the remdesivir or a pharmaceutically acceptable salt thereof comprised by the medically active liquid and to be administered to a patient or subject in need thereof may be determined according to routine experimentation as known to those of skill in the art.

The medically active liquid comprising remdesivir or a pharmaceutically acceptable salt thereof to be administered according to the method of the present invention may be administered in 1 single or several separate doses by inhalation, such as 1 to about 6 or 4 doses per day, or 2 or 3 doses per day using an inhaler or inhalation device as described in further detail below.

According to the method of the present invention, the medically active liquid comprising remdesivir or a pharmaceutically acceptable salt thereof is administered to a subject in need thereof in nebulized form using an inhalation device. The term 'in nebulized form' as used herein means, with regard to the medically active liquid to be administered, that the medically active liquid is present in the form of an aerosol in which the medically active liquid comprising remdesivir or a pharmaceutically acceptable salt thereof is present in the form of finely divided particles or droplets dispersed in air or another propellant as the continuous phase.

In specific embodiments, such an aerosol has respirable particles or droplets, preferably having a mass median aerodynamic diameter (as measured by laser diffraction) of not more than about 10 µm, in particular not more than about 7 µm, or not more than about 5 µm, respectively.

In further specific embodiments, the remdesivir or a pharmaceutically acceptable salt thereof comprised by the medically active liquid is administered to the lungs of the subject, specifically in form of a respirable aerosol comprising the remdesivir or a pharmaceutically acceptable salt thereof.

In further specific embodiments, the medically active liquid to be administered by the method of the present invention may be essentially free of a propellant.

According to the method of the present invention, the medically active liquid comprising remdesivir or a pharmaceutically acceptable salt thereof is administered to a subject in need thereof using an inhalation device. The term 'inhalation device' as used herein is to be understood in the broadest sense as referring to a device that allows and is adapted for the nebulization in inhalative administration, preferably by oral inhalation, of a medically active liquid. Examples of such inhalation devices are known to those of skill in the art and comprise, but are not limited to, e.g. metered dose inhalers (MDI), nebulizers, vibrating mesh inhalers and soft-mist-inhalers (SMI). Exemplary embodiments of suitable inhalers for the administration of the medically active liquid comprising remdesivir or a pharmaceutically acceptable salt thereof are described, e.g., in "Inhalation drug delivery devices: technology update" Medical Devices: Evidence and Research 2015:8131-139; or "Recent advances in in aerosolized drug delivery", A. Chandel et al., Biomedicine & Pharmacotherapy, Vol. 112, April 2019, 108601 (https://do.org/j.biopha.2019.108601), or in "Pharmaceutical Inhalation Aerosol Technology", Third Edition, A. J. Hickey et al., May 1, 2019, the contents of each of which are herein incorporated by reference in their entireties.

In specific embodiments, such nebulization and administration by inhalation of the medically active liquid comprising remdesivir or a pharmaceutically acceptable salt thereof can be performed using a hand-held inhalation device.

In further specific embodiments, the inhalation device that may be used to administer the medically active liquid comprising remdesivir or a pharmaceutically acceptable salt thereof is a soft-mist-inhaler. The term 'soft-mist-inhaler' as used herein, in specific embodiments, refers to a non-electrified mobile inhalation device for liquid formulations with low velocity nebulization properties. In further specific embodiments, such inhalation device or, more specifically, such soft-mist inhaler comprises at least one impingement-type nozzle as described in further detail below for the nebulization/aerosolization of the medically active liquid.

Suitable inhalation devices are known such as, e.g. the Respimat® inhaler (Boehringer Ingelheim), vibrating membrane nebulizers such as eFlow® (PARI), Vibrating-Mesh® nebulizers (such as Philips innoSpire Go) and others.

A further exemplary suitable inhalation device is known, e.g., from document EP 0 627 230 B1, the contents of which are incorporated herein by reference in its entirety. Essential components of this exemplary inhalation device are a reservoir in which the medically active liquid that is to be aerosolized is contained; a pumping device for generation of a pressure being sufficiently high for nebulizing; as well as an atomizing device in the form of a nozzle. By means of the pumping device, the liquid is drawn in a discrete amount, i.e., not continuously, from the reservoir, and fed to the nozzle. The pumping device works without propellant and generates pressure mechanically.

A further exemplary embodiment of a suitable inhalation device is described in document WO 91/14468 A1, the contents of which are herein incorporated by reference in its entirety. In such a device, the pressure in the pumping chamber which is connected to the housing is generated by movement of a moveable hollow piston. The piston is moveably arranged inside the immobile cylinder or pumping chamber. The (upstream arranged) inlet of the hollow piston is fluidically connected to the interior of the reservoir (reservoir pipe section). Its (downstream arranged) tip leads into the pumping chamber. Furthermore, a check valve that inhibits a back flow of liquid into the reservoir is arranged inside the tip of the piston.

Soft-mist inhalers as described above have been proven as a very effective means for providing medically active liquids or compositions or pharmaceutically active compounds contained therein into the lungs of a patient or subject in need thereof. Such a soft mist inhaler usually comprises one or a plurality of impingement-type nozzles. Such an impingement-type nozzle is adapted to emit at least two jets of liquid which are directed such as to collide and break up into small aerosol droplets of the medically active liquid to nebulized. The nozzle or nozzles usually are firmly affixed to the user-facing side of the housing of the inhalation device in such a way that it is immobile, or non-moveable, relative to the housing or at least relative to the side or part of the housing which faces the user (e.g., patient) when the device is used.

A specific embodiment of such a soft mist inhaler which is suitable for the administration of the medically active liquid comprising remdesivir or a pharmaceutically acceptable salt thereof is described, e.g., in international patent application WO 2018/197730 A1, the contents of which are incorporated herein by reference in its entirety. It should be noted, however, that the inhaler device described therein is just one example of a suitable inhaler device to be used according to the present invention and, therefore should not be interpreted as limiting the scope of the invention in any respect.

In specific embodiments of the method according to the present invention, the inhalation device that may be used to administer the medically active liquid comprising remdesivir or a pharmaceutically acceptable salt thereof is a hand-held inhalation device for delivering a nebulised medically active aerosol for inhalation therapy, comprising
  (a) a housing having a user-facing side;
  (b) an impingement-type nozzle for generating the nebulised aerosol by collision of at least two liquid jets, the nozzle being firmly affixed to the user-facing side of the housing such as to be immobile relative to the housing;
  (c) a fluid reservoir arranged within the housing; and
  (d) a pumping unit arranged within the housing, the pumping unit having
    an upstream end that is fluidically connected to the fluid reservoir;
    a downstream end that is fluidically connected to the nozzle;
    wherein the pumping unit is adapted for pumping fluid from the fluid reservoir to the nozzle;
    wherein the pumping unit further comprises
    (i) a riser pipe having an upstream end, wherein the riser pipe is adapted to function as a piston in the pumping unit, and firmly affixed to the user-facing side of the housing such as to be immobile relative to the housing; and (ii) a hollow cylinder located upstream of the riser pipe, wherein the upstream end of the riser pipe is inserted in the cylinder such that the cylinder is longitudinally movable on the riser pipe;

(iii) a lockable means for storing potential energy when locked and for releasing the stored energy when unlocked, the means being arranged outside of, and mechanically coupled to, the cylinder such that unlocking the means results in a propulsive longitudinal movement of the cylinder towards the downstream end of the pumping unit.

In specific embodiments, such a preferred inhalation device comprises a housing having a user-facing side, an impingement-type nozzle for generating the nebulised aerosol by collision of at least two liquid jets, a fluid reservoir arranged within the housing, and a pumping unit which is also arranged within the housing. The nozzle may be firmly affixed to the user-facing side of the housing such as to be immobile relative to the housing. The pumping unit may have an upstream end that is fluidically connected to the fluid reservoir and a downstream end that is fluidically connected to the nozzle. Furthermore, the pumping unit is adapted for pumping fluid from the fluid reservoir to the nozzle, and it comprises a riser pipe which is adapted to function as a piston in the pumping unit, a hollow cylinder and a lockable means for storing potential energy. The riser pipe is preferably firmly affixed to the user-facing side of the housing such as to be immobile relative to the housing. The hollow cylinder is located upstream of the riser pipe, and the upstream end of the riser pipe is inserted in the cylinder such that the cylinder is longitudinally movable on the riser pipe. The lockable means is capable of storing potential energy when locked and is adapted for releasing the stored energy when unlocked. The lockable means is arranged outside of, and mechanically coupled to, the cylinder in such a way that unlocking the means results in a propulsive longitudinal movement of the cylinder towards the downstream end of the pumping unit.

As used herein, a hand-held inhalation device is a mobile device which can be conveniently held in one hand and which is suitable for delivering a nebulised medically active aerosol for inhalation therapy. In order to be suitable for inhalation therapy, the device must be able to emit a medically active aerosol whose particle size is respirable, i.e., small enough to be taken up by the lungs of a patient or user, as already outlined above. Typically, respirable particles have a mass median aerodynamic diameter of not more than about 10 µm, in particular not more than about 7 µm, or not more than about 5 µm, respectively. In this respect, inhalation devices are substantially different from devices that emits spray for oral or nasal administration, such as disclosed in US 2004/0068222 A1, the contents of which are herein incorporated by reference in its entirety.

In some embodiments, the average particle size distribution of the nebulised medically active aerosol comprising remdesivir is about 1.0 µm to about 2.0 µm at the Dv10. In other embodiments, the average particle size distribution of the nebulised medically active aerosol comprising remdesivir is about 2.0 µm to about 4.0 µm at the Dv50. In yet other embodiments, the average particle size distribution of the nebulised medically active aerosol comprising remdesivir is about 4.0 µm to about 10.0 µm at the Dv90. The terms "Dv10, Dv50, and Dv90" refer to the maximum particle diameter in micrometers (µm) where 10%, 50%, and 90%, respectively, of which the sample volume exists.

The inhalation device that may be used in the method of the present invention is capable of delivering a nebulised aerosol. As used herein, an aerosol is a system having at least two phases: a continuous phase which is gaseous, and which comprises a dispersed liquid phase in the form of small liquid droplets. Optionally, the liquid phase may itself represent a liquid solution, dispersion, suspension, or emulsion.

A suitable nozzle is important for the generation of a nebulised aerosol. According to the invention, the nozzle preferably is of the impingement type. This means that the nozzle is adapted to emit at least two jets of liquid which are directed such as to collide and break up into small aerosol droplets. The nozzle may be firmly affixed to the user-facing side of the housing of the inhalation device in such a way that it is immobile, or non-moveable, relative to the housing or at least relative to the side or part of the housing which faces the user (e.g., patient) when the device is used.

The fluid reservoir which may be arranged within the housing is preferably adapted to hold or store the medically active liquid from which the nebulised aerosol is generated and delivered by the inhalation device.

The pumping unit which may also be arranged within the housing is preferably adapted to function as a piston pump, also referred to as plunger pump, wherein the riser pipe functions as the piston, or plunger, which is longitudinally moveable within the hollow cylinder. The inner segment of the hollow cylinder in which the upstream end of the riser pipe moves may form a pumping chamber which has a variable volume, depending on the position of the riser pipe relative to the cylinder.

The hollow cylinder which provides the pumping chamber may be fluidically connected with the fluid reservoir, either directly or indirectly, such as by means of an optional reservoir pipe (or reservoir pipe section). Similarly, the riser pipe, whose reservoir-facing, interior (upstream) end which can be received in the hollow cylinder, may be fluidically connected at its downstream or exterior end to the nozzle in a liquid-tight manner, either directly or indirectly.

In this context, the expression "hollow cylinder" refers to a part or member which is hollow in the sense that it comprises an internal void which has a cylindrical shape, or which has a segment having a cylindrical space. In other words, and as is applicable to other types of piston pumps, it is not required that the external shape of the respective part or member is cylindrical. Moreover, the expression "hollow cylinder" does not exclude an operational state of the respective part or member in which the "hollow" space may be filled with material, e.g., with a liquid to be nebulised.

As used herein, a longitudinal movement is a movement along the main axis of the hollow cylinder, and a propulsive movement is a movement of a part in a downstream (or forward) direction.

In some embodiments, the riser pipe of the pumping unit of the inhalation device of the invention is arranged downstream of the cylinder, and it is preferably firmly affixed to the user-facing side of the housing such as to be immobile relative to the housing or at least to the part of the housing which comprises the user-facing side of the housing. For the avoidance of doubt, in this context firmly fixed means either directly or indirectly (i.e., via one or more connecting parts) fixed such as to prevent relative movement between the respective parts. As the nozzle is also immobile relative to the housing or the respective part of the housing, the riser pipe is also immobile relative to the nozzle, and the pumping action is affected by the longitudinal movement of the hollow cylinder. A propulsive movement of the cylinder, which is arranged in an upstream position relative to the riser pipe, results in a decrease of the volume of the pumping chamber, and a repulsive movement of the cylinder results in an increase of the volume. In other words, the riser pipe maintains its position relative to the housing, and the hollow cylinder can alter its position relative to the housing, and in particular, along a longitudinal axis of the same, such as to perform a piston-in-cylinder-type movement of the immobile riser pipe in the moveable cylindrical member.

This arrangement differs from other impingement-type inhalation devices which rely on a pumping unit whose riser pipe is in an upstream position and a cylindrical member in a downstream position wherein the riser pipe is moveable and the cylindrical member is fixed to the housing, as disclosed in US 2012/0090603 A1, the contents of which are incorporated herein by reference in its entirety. It should be noted, however, that inhalation devices with this type of pumping may also be suitable for the nebulization an inhalative administration of the medically active liquid according to the method of the present invention.

A key advantage of the described preferred inhalation device is that the passage between pumping chamber and fluid reservoir can be designed with less restrictions with respect to its dimensions. It is, for example, possible to accommodate a significantly larger inlet valve (also referred to as check valve), which is easier to manufacture since it does not have to be contained within a narrow riser pipe. Instead, the arrangement allows the use of a check valve whose size is only restricted by the interior size of the housing or the dimensions of the means for storing potential energy. In other words, the diameters of the valve, the riser pipe and—if used—the reservoir pipe do not need to match each other. Furthermore, since no movable piston needs to be connected to the fluid reservoir, the component which provides the fluid connection to the reservoir can be designed independently of the moveable component, i.e., the hollow cylinder, allowing the individual parts to be adapted to suit their respective individual functions. In this respect, the described pump arrangement provides for higher design flexibility because the moveable hollow cylinder, due to its robust structure and dimensions, provides better opportunities for designing a mechanically stable connection with the reservoir than would a less robust moveable riser pipe. Also, the connection between the hollow cylinder and the fluid reservoir can be designed with a larger diameter, such that higher flow velocities and fluid viscosities become feasible. Further, a support for the reservoir can be integrated into any component that comprises the cylinder. Additionally, any vent for pressure equilibration of the reservoir can be moved away from the reservoir body itself to a connector which forms an interface between reservoir and hollow cylinder, thus facilitating construction and avoiding the necessity to provide an essentially "open" reservoir body.

As mentioned, the lockable means for storing potential energy may be adapted to store energy in its locked state and to release the stored energy when unlocked. The means may be mechanically coupled to the hollow cylinder in such a way such that unlocking the means results in a propulsive longitudinal movement of the cylinder towards the downstream end of the pumping unit. During this movement, the internal volume of the cylinder, i.e., the volume of the pumping chamber, decreases. Vice versa, when the means for storing potential energy is in the locked state, the hollow cylinder is in its most upstream position in which the volume of the pumping chamber is largest. The locked state could also be considered a primed state. When the state of the means for storing energy is altered from the unlocked to the locked state, which could be referred to as priming the device, the hollow cylinder performs a repulsive longitudinal movement, i.e., from its most downstream position towards its most upstream position. A pumping cycle usually consists of two subsequent and opposing movements of the cylinder starting from its most downstream position to its most upstream (or primed) position and—driven by the means for storing potential energy that now releases its energy—back to its most downstream position.

In one of the preferred embodiments of the described inhalation device, the pumping unit is a high-pressure pumping unit and adapted to operate, or to expel fluid, at a pressure of at least about 50 bar. In other preferred embodiments, the operating pressure of the pumping unit is at least about 10 bar, or at least about 100 bar, or from about 2 bar to about 1000 bar, or from about 50 bar to about 250 bar, respectively. As used herein, the operating pressure is the pressure at which the pumping unit expels fluid, in particular a medically active liquid, such as an inhalable aqueous liquid formulation of a pharmacologically active ingredient, from its pumping chamber in a downstream direction, i.e. towards the nozzle. In this context, the expression "adapted to operate" means that the components of the pumping unit are selected with respect to the materials, the dimensions, the quality of the surfaces and the finish are selected such as to enable operation at the specified pressure.

Moreover, such high-pressure pumping unit implies that the means for storing potential energy is capable of storing and releasing a sufficient amount of energy to drive the propulsive longitudinal movement of the cylinder with such a force that the respective pressure is obtained.

The means for the storage of potential energy may be designed as a tension or pressure spring. Alternatively, besides a metallic or plastic body, also a gaseous medium, or magnetic force utilizing material can be used as means for energy storage. By compressing or tensioning, potential energy is fed to the means. One end of the means is supported at or in the housing at a suitable location; thus, this end is essentially immobile. With the other end, it is connected to the hollow cylinder which provides the pumping chamber; thus, this end is essentially moveable. The means can be locked after being loaded with a sufficient amount of energy, such that the energy can be stored until unlocking takes place. When unlocked, the means can release the potential energy (e.g., spring energy) to the cylinder with the pumping chamber, which is then driven such as to perform a (in this case, longitudinal) movement. Typically, the energy release takes place abruptly, so that a high pressure can build up inside the pumping chamber before a significant amount of liquid is emitted, which results in a pressure decrease. In fact, during a significant portion of the ejection phase, an equilibrium exists of pressure delivered by the means for the storage of potential energy, and the amount of already emitted liquid. Thus, the amount of liquid remains essentially constant during this phase, which is a significant advantage to devices which use manual force of the user for the emission, such as the devices disclosed in documents US 2005/0039738 A1, US 2009/0216183 A1, US 2004/0068222 A1, or US 2012/0298694 A1, the contents of each of which are incorporated by reference in their entireties, since manual force depends on the individual user or patient and is very likely to vary largely during the ejection phase, resulting in inhomogeneous droplet formation, size, and amount. In contrast to the prior art, the means according to the invention ensures that the inhalation device delivers highly reproducible results.

The means for storing potential energy may also be provided in the form of a highly pressurized gas container. By suitable arrangement and repeatable intermittent activating (opening) of the same, part of the energy which is stored inside the gas container can be released to the cylinder. This process can be repeated until the remaining energy is insufficient for once again building up a desired pressure in the pumping chamber. After this, the gas container must be refilled or exchanged.

In one of the preferred embodiments, the means for storing potential energy is a spring having a load of at least 10 N in a deflected state. In a particularly preferred embodiment, the means for storing potential energy is a compression spring made of steel having a load from about 1 N to about 500 N in its deflected state. In other preferred embodiments, the compression spring from steel has a load from about 2 N to about 200 N, or from about 10 N to about 100 N, in its deflected state.

The inhalation device that may be used in the method of the present invention is preferably adapted to deliver the nebulised medically active aerosol in a discontinuous manner, i.e., in the form of discrete units, wherein one unit is delivered per pumping cycle. In this aspect, the device differs from commonly known nebulisers such as jet nebulisers, ultrasonic nebulisers, vibrating mesh nebulisers, or electrohydrodynamic nebulisers which typically generate and deliver a nebulised aerosol continuously over a period of several seconds up to several minutes, such that the aerosol requires a number of consecutive breathing manoeuvres in order to be inhaled by the patient or user. Instead, an inhalation device suitable for the administration of the medically active liquid according to the present invention is preferably adapted to generate and emit discrete units of aerosol, wherein each of the units corresponds to the amount (i.e., volume) of fluid (i.e., medically active liquid) which is pumped by the pumping unit in one pumping cycle into the nozzle where it is immediately aerosolised and delivered to the user or patient. Vice versa, the amount of medically active liquid pumped by the pumping unit in one pumping cycle determines the amount of the pharmacologically active agent which the patient receives per dosing. It is therefore highly important with respect to achieving the desired therapeutic effect that the pumping unit operates precisely, reliably and reproducibly. The inventors have found that the inhalation device incorporating the pumping unit as described above is particularly advantageous in that it does exhibit high precision and reproducibility.

In one preferred embodiment, a single dose of the medication (i.e., of the nebulised aerosol of the medically active liquid) is contained in one unit, i.e., in the volume that is delivered from the pumping unit to the nozzle for aerosol generation in one single pumping cycle. In this case, the user or patient will prime and actuate the device only once, and inhale the released aerosol in one breathing maneuver, per dosing (i.e., per dosing event).

In another preferred embodiment, a single dose of the medication consists of two units of the aerosol, and thus requires two pumping cycles. Typically, the user or patient will prime the device, actuate it such as to release and inhale a unit of the aerosol, and then repeat the procedure. Alternatively, three or more aerosol units may constitute a single dosing.

The volume of fluid (e.g., of medically active liquid) that is pumped by the pumping unit in one pumping cycle is preferably in the range from about 2 to about 150 µl. In particular, the volume may range from about 0.1 to about 1000 µl, or from about 1 to about 250 µl, respectively. These volume ranges are nearly the same as the volume of liquid phase that is contained in one unit of aerosol generated by the inhalation device, perhaps with minor differences due to minute losses of liquid in the device.

In another preferred embodiment, the pumping unit of the inhalation device comprises an inlet valve, also referred to as a check valve or inlet check valve, positioned in the hollow cylinder. According to this embodiment, the interior space of the hollow cylinder, i.e., the pumping chamber, is fluidically connected with the fluid reservoir via the inlet check valve. The inlet valve allows the inflow of liquid into the pumping chamber, but prevents the backflow of liquid towards, or into, the fluid reservoir. The position of the inlet valve may be at or near the upstream end of the cylinder such as to make nearly the entire internal volume of the hollow cylinder available for functioning as the pumping chamber. Alternatively, it may be more centrally located along the (longitudinal) main axis of the hollow cylinder such as to define an upstream segment and a downstream segment of the cylinder, the upstream segment being upstream of the inlet valve and the downstream segment being downstream of the valve. In this case the pumping chamber is located in the downstream segment.

As mentioned, one of the advantageous effects is that an inlet valve having relatively large dimensions may be accommodated in this position, i.e., at the upstream end of the pumping chamber. This is particularly beneficial as it allows for large dimensions of the fluid conduit(s) within the valve, thus enabling high fluid velocities which translate into a rapid filling of the pumping chamber during the priming of the inhalation device. Moreover, the use of liquids having a higher viscosity than ordinary liquid formulations for inhalation, such as highly concentrated solutions of soluble active ingredients, become feasible for inhalation therapy.

According to a further preferred embodiment, the inlet valve may be adapted to open only when the pressure difference between the upstream and the downstream side of the valve, i.e., the fluid reservoir side and the pumping chamber side, is above a predefined threshold value, and remains closed as long as the pressure difference is below the threshold value. The term 'pressure difference' as used in this context means that, irrespective of the absolute pressure values, only the relative pressure difference between the two sides is relevant for determining whether the valve blocks or opens. If, for example, the pressure on the upstream (reservoir) side is already positive (e.g., 1.01 bar due to thermal expansion), but the pressure on the downstream (pumping chamber) side is ambient pressure (1.0 bar, no activation of the device), the pressure difference (here: 0.01 bar) is below the threshold value (e.g., 20 mbar), which allows the valve to stay closed even when subject to a positive pressure in opening direction. This means that the check valve remains closed until the threshold pressure is met, thus keeping the passage between reservoir and pumping chamber safely shut e.g. when the inhalation device is not in use. Examples for threshold pressure differences are in the range of 1 to 1000 mbar, and more preferably between about 10 and about 500 mbar, or between about 1 and about 20 mbar.

When actuating the inhalation device, as the means for storing potential energy alters its state from a locked state to an unlocked state, energy may be released which effects the cylinder to perform its propulsive longitudinal movement, significant pressure is built up in the pumping chamber. This generates a marked pressure difference (due to a high pressure in the pumping chamber and a substantially lower pressure in the fluid reservoir) which exceeds the threshold value of the pressure difference, so that the check valve opens and allows the pressure chamber to become filled with liquid from the reservoir.

A valve type that may be designed to operate with such a threshold pressure difference is, e.g., a ball valve pre-loaded with a spring. The spring pushes the ball into its seat, and only if the pressure acting against the spring force exceeds the latter, the ball valve opens. Other valve types which—depending on their construction—may operate with such a threshold pressure difference are duckbill valves or flap valves.

The advantage of such a valve operating with a threshold pressure difference is that the reservoir can be kept closed until active use is being made of the inhalation device, thus reducing unwanted splashing of reservoir liquid during device transport, or evaporation during long-term storage of the device.

In a further preferred embodiment, the inhalation device that may be used in the method according to the invention further comprises an outlet valve inside the riser pipe, or at an end of the riser pipe, for avoiding a return flow of liquid or air from the riser pipe into the hollow cylinder. In many cases, the use of such outlet valve will prove to be advantageous. Typically, the downstream end of the riser pipe is located close to the nozzle. The nozzle is in fluidic communication with the outside air. After emitting in aerosolised form, the amount of liquid which is delivered from the pumping unit through the nozzle, driven by the propulsive longitudinal movement of the cylinder, the pumping chamber must be refilled. For this purpose, it slides back on the riser pipe into its previous upstream position (i.e., performs a repulsive longitudinal movement), so that the interior volume of the pumping chamber increases. Along with this, a negative pressure (sometimes also referred to as "underpressure") is generated inside the pumping chamber which causes liquid to be sucked into the pumping chamber from the fluid reservoir which is located upstream of the pumping chamber. However, such negative pressure may also propagate downstream through the riser pipe up to the outside of the nozzle and could lead to air being sucked into the device through the nozzle, or nozzle openings, respectively. This problem can be avoided by providing an outlet valve, also referred to as outlet check valve, which opens towards the nozzle openings and blocks in the opposite direction.

Optionally, the outlet valve is of a type that blocks below (and opens above) a threshold pressure difference as described in the context of the inlet valve above. If a ball valve with a spring is used, the spring force must be directed against the pumping chamber such that when the difference between the interior pressure of the pumping chamber and the ambient pressure exceeds the threshold pressure difference value, the outlet valve opens. The advantages of such a valve correspond to the respective aforementioned advantages.

As mentioned, the outlet valve may be positioned within the riser pipe. Alternatively, the inhalation device may comprise an outlet valve which is not integrated within the riser pipe, but positioned at or near one of the ends of the riser pipe, in particular at or near its downstream end, e.g., in a separate connector between the riser pipe and the nozzle. This embodiment may be advantageous in certain cases, e.g., if there is a need for a riser pipe with a particularly small diameter which makes the integration of a valve difficult. By accommodating the outlet valve downstream of the riser pipe, a valve with a relatively large diameter may be used, thus simplifying the requirements for the valve design.

In a further alternative embodiment, the outlet valve is absent. This embodiment may be feasible as the fluid channels of an impingement-type nozzle may have relatively small cross sections, resulting in only minor or very slow back flow at the given pressure conditions during the priming of the device. If the amount of backflow is considered acceptable in view of a particular product application, the inhaler design may be simplified by avoiding the outlet valve.

In any case, whether the inhalation device is designed with or without an outlet valve, all other options and preferences described with respect to other device features are applicable to both of these alternative embodiments.

In a further preferred embodiment, the inhalation device according to the invention comprises a fluid reservoir which is firmly attached to the hollow cylinder such as to be moveable together with the hollow cylinder inside the housing. This means that in each ejection phase of the pumping cycle, the fluid reservoir moves together with the hollow cylinder from an initial ("upstream") position, in which the pumping chamber has its maximum interior volume, towards an end ("downstream") position, in which the volume of the pumping chamber is minimal; and during the subsequent "priming" step, the fluid reservoir returns together with the hollow cylinder to their initial ("upstream") position.

As used herein, the expression "firmly attached" includes both permanent and non-permanent (i.e., releasable) forms of attachment. Moreover, it includes direct and indirect (i.e., via one or more connecting parts) types of attachment. At the same time, as mentioned above, "firmly attached" means that the respective parts are fixed to each other in such a way as to substantially prevent their movement relative to each other. In other words, two parts that are firmly attached to each other may only be movable together, and with respect to each other, they are non-movable or immobile.

One of the advantages of this embodiment wherein the fluid reservoir is firmly attached to the hollow cylinder is that it provides the smallest possible dead volume between the reservoir and the pumping chamber.

According to an alternative embodiment, the fluid reservoir is fluidically connected to the hollow cylinder by means of a flexible tubular element, and firmly attached to the housing. According to this embodiment, the reservoir is not firmly attached to the hollow cylinder and does not move along with it when the cylinder performs its longitudinal movements. Instead, it is firmly, but optionally detachably, directly or indirectly, attached to the housing or to a part of the housing. One advantage of this embodiment is that the energy which is abruptly released upon unlocking the means for storing potential energy solely acts on the hollow cylinder and not on the fluid reservoir. This may be particularly advantageous in cases in which the fluid reservoir in its initial (fully filled state) at the beginning of its usage has a relatively large mass which decreases overuse. A higher acceleration of the hollow cylinder would translate into a higher pressure in the pumping chamber.

For the avoidance of doubt, all other options and preferences described herein-above and below with respect to other device features are applicable to both of these alternatives, i.e., regardless of whether the fluid reservoir is firmly attached to the hollow cylinder or not.

In one embodiment, the fluid reservoir is designed to be collapsible, such as by means of a flexible or elastic wall.

The effect of such design is that upon repeated use of the device which involves progressive emptying of the reservoir, the flexible or elastic wall buckles or folds such as to reduce the internal volume of the reservoir, so that the negative pressure which is necessary for extraction of a certain amount of liquid is not required to increase substantially over the period of use. In particular, the reservoir may be designed as a collapsible bag. The advantage of a collapsible bag is that the pressure inside the reservoir is almost independent of the filling level, and the influence of thermal expansion is almost negligible. Also, the construction of such a reservoir type is rather simple and already well established.

A similar effect can be achieved with a rigid container which has a moveable bottom (or wall) by means of which the interior volume of the reservoir can also be successively reduced.

In a second aspect, the present invention provides for a medically active liquid comprising remdesivir or a pharmaceutically acceptable salt thereof for use in the treatment of a viral infection or viral disease, disorder or condition in a subject, wherein the medically active liquid is administered in nebulized form using an inhalation device. In some embodiments, the viral disease, disorder or condition is a respiratory disease, disorder or condition.

In a third aspect, the present invention provides for the use of remdesivir or a pharmaceutically acceptable salt thereof for the preparation of a medically active liquid for the treatment of a viral infection or viral disease, disorder or condition in a subject, wherein the medically active liquid is administered to the subject in nebulized form by inhalation using an inhalation device. In some embodiments, the viral disease, disorder or condition is a respiratory disease, disorder or condition.

In a fourth aspect, the present invention provides for the use of an inhalation device for the treatment of a viral infection or viral disease, disorder or condition in a subject, wherein the medically active liquid is administered in nebulized form using the inhalation device and wherein the medically active liquid comprises remdesivir or a pharmaceutically acceptable salt thereof. In some embodiments, the viral disease, disorder or condition is a respiratory disease, disorder or condition.

It should be noted that all embodiments, features and combinations thereof disclosed above in connection with the method of the first aspect of the invention apply equally to all further aspects of the invention.

DETAILED DESCRIPTION OF THE DRAWINGS

In FIG. 1, one of the preferred embodiments of an inhalation device useful for the method according to the present invention is depicted schematically and not-to-scale. FIG. 1 shows the situation prior to first use.

The inhalation device comprises a housing (1), which is preferably shaped and dimensioned such that it can be held with one hand and can be operated by one finger, e.g. a thumb or index finger (not shown). A fluid reservoir (2) for the storage of the medically active liquid (F) to be administered according to the present invention is located inside the housing (1). The depicted reservoir (2) is designed to be collapsible so that in the course of the emptying of the reservoir by the repeated use of the device, the soft or elastic walls deform such that the negative pressure required for withdrawing liquid from the reservoir remains substantially constant over time. A similar effect could be achieved with a rigid container that has a movable bottom by means of which the interior volume of the reservoir can also be successively be reduced (not shown).

Furthermore, the shown inhalation device comprises a pumping unit with a hollow cylinder (9) within the housing (1) which forms a pumping chamber (3) for the generation of the desired pressure which is necessary for emitting liquid (F) (i.e. the medically active liquid) and nebulising the same. The pumping unit may also comprise further components not depicted in the drawing, such as a push button, locking device, etc.

As a means for the storage of potential energy (7), a spring is provided which is coupled with one end (upwards directed, or downstream) to the cylinder (9) and which is supported at the housing (1) (lower part of the figure).

The shown inhalation device further comprises a riser pipe (5) with at least one reservoir-facing, or upstream, interior end (5A) which can be received in said cylinder (9). In other words, riser pipe (5) can be at least partially pushed into hollow cylinder (9), resulting in a decrease of the interior volume of pumping chamber (3). The term "interior volume" describes the volume of the space which extends from the reservoir-facing inlet of the cylinder (9) to the place where the interior end (5A) of the riser pipe (5) is located. In the depicted situation, riser pipe (5) is almost entirely contained in the cylinder (9). As a result, the interior volume of the pumping chamber (3), situated between inlet valve (4) and the interior end (5A) of riser pipe (5), is at a minimum.

Preferably, the section (or segment) of the hollow cylinder (9) which serves as, or accommodates, the pumping chamber (3) and which receives the riser pipe (5) exhibits a circular inner cross-section whose diameter relatively closely (e.g. except for a small gap) matches the diameter of the circular outer cross-section of the corresponding segment of the riser pipe (5). Of course, other (e.g. non-circular) cross section shapes are possible as well.

According to the depicted embodiment, inlet valve (4) is arranged between reservoir (2) and inlet of the pumping chamber (3) formed by the cylinder (9).

Furthermore, the inhalation device comprises a nozzle (6) which is connected liquid-tight to the exterior (or downstream) end (5B) of the riser pipe (5). Nozzle (6) is an impingement-type nozzle for generating the nebulised aerosol by collision of at least two liquid jets. Preferably, the cross sections of the liquid-containing channels are relatively small, typically in the region of microns.

Also depicted is an optional outlet valve (8) inside the riser pipe (5) for avoiding a backflow of liquid or air into the exterior end (58) of the same from the outside. Outlet valve (8) is arranged in the interior end (5A) of riser pipe (5). Liquid (F) can pass outlet valve (8) in direction of nozzle (6), but outlet valve (8) blocks any undesired backflow in the opposite direction.

As can be seen in FIG. 1, riser pipe (5) is designed immobile with respect to the housing (1), and firmly attached to housing (1), indicated by the connection in the region of exterior end (5B) with housing (1). Riser pipe (5) is also firmly attached to nozzle (6), which, in turn, is attached to housing (1) as well. In contrast, the hollow cylinder (9) providing the pumping chamber (3) is designed to be moveable with respect to housing (1) and nozzle (6). The benefits of this design have been explained; reference is made to the respective sections of the description above.

Figure 2:
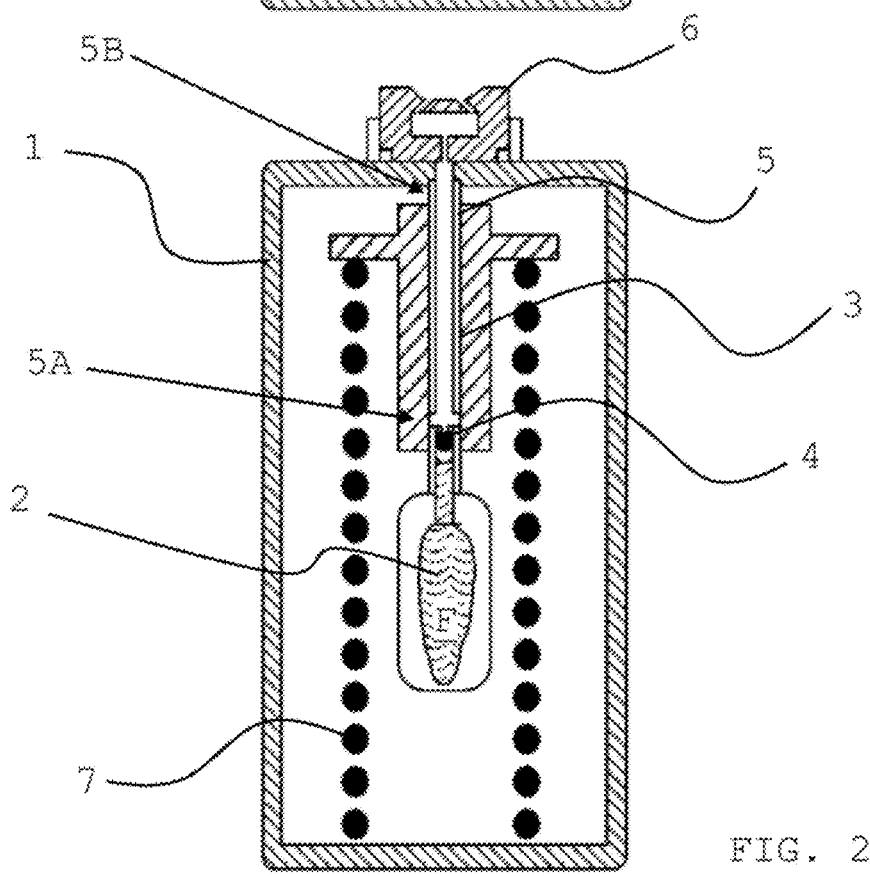
FIG. 2 shows an inhalation device similar to the one of FIG. 1, but without an outlet valve.

Referring to FIG. 2, a device similar to the one of FIG. 1 is depicted. However, the embodiment shown in FIG. 2 lacks the (optional) outlet valve (8). All other components are present, and also the function is comparable. In this embodiment, pumping chamber (3) extends from downstream of the valve (4) up to nozzle (6), which is the location where the fluidic resistance increases significantly. In an alternative embodiment having a particularly small inner diameter of riser pipe (5), pumping chamber (3) extends only from downstream of the valve (4) up to upstream interior end (5A) of riser pipe (5).

Figure 3:
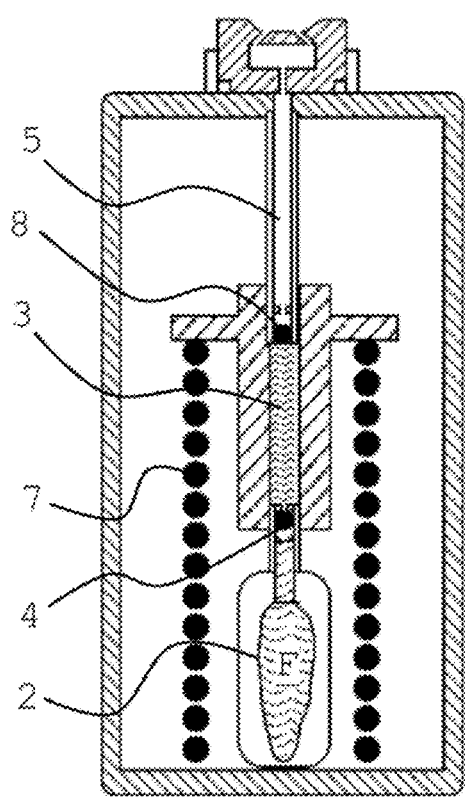
FIG. 3 shows the embodiment of FIG. 1 with a filled pumping chamber.

FIG. 3 shows the embodiment of FIG. 1 with a filled pumping chamber. The hollow cylinder (9) has been moved to its most upstream position, thereby loading the means for the storage of potential energy (7). Outlet valve (8) is closed due to negative pressure inside pumping chamber (3), and the inlet valve (4) is open towards the fluid reservoir (2). Increasingly collapsing walls of reservoir (2) allow the internal pressure in the reservoir (2) to remain nearly constant, while the pressure inside the pumping chamber (3) drops because of the propulsive longitudinal motion of the hollow cylinder (9), thus increasing the volume of pumping chamber (3). As a result, the pumping chamber (3) has been filled with the medically active liquid (F) from the reservoir (2).

Figure 4:
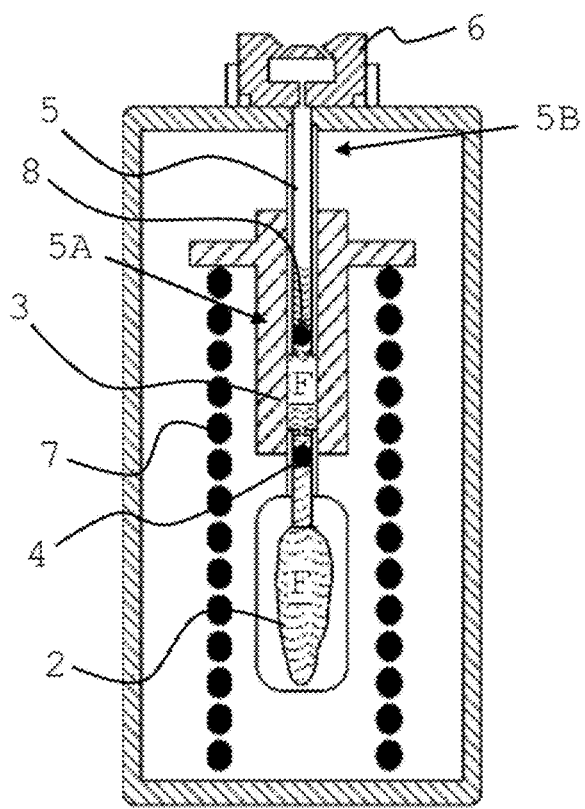
FIG. 4 shows the situation during the first actuation of the inhalation device of FIG. 1.

In FIG. 4, the situation after the first actuation of the inhalation device of FIG. 1 is shown. The means for the storage of potential energy (7) has been released from the loaded position as shown in FIG. 3. It pushes the cylinder (9) in a downstream direction such as to slide over the riser pipe (5). The interior end (5A) of the riser pipe (5) has come closer to the inlet check valve (4) which is now closed. As a result, the pressure inside the pumping chamber (3) rises and keeps the inlet valve (4) closed but opens outlet valve (8). Liquid (F) flows from the riser pipe (5) through its exterior end (5B) towards nozzle (6).

Figure 5:
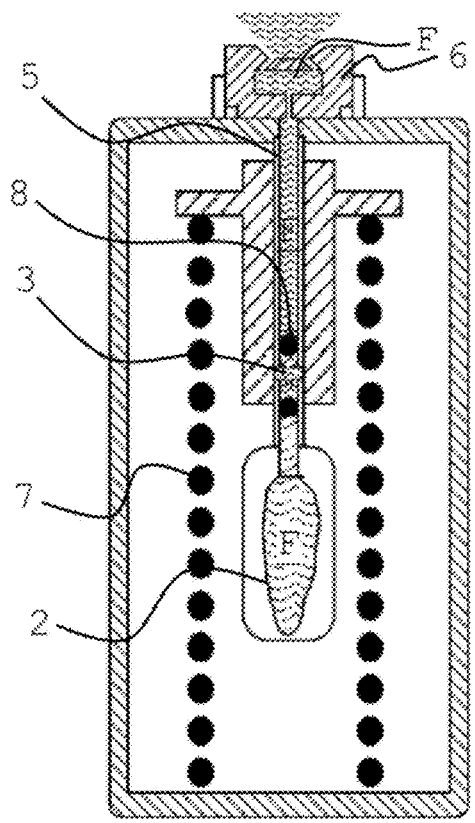
FIG. 5 shows the situation at the end of the first actuation.

FIG. 5 shows the inhalation device of FIG. 1 in the situation at the end of the aerosol emission phase. The means for the storage of potential energy (7) is in its most relaxed end position (spring fully extended). Also, the hollow cylinder (9) has been pushed almost entirely onto riser pipe (5) such that the interior volume of pumping chamber (3) has reached its minimum. Most of the liquid (F) previously contained in the pumping chamber (3) has passed outlet valve (8) into the main segment of the riser pipe (5). Some liquid (F) has been pushed towards, and though, nozzle (6), where nebulisation takes place, such that a nebulised aerosol is emitted towards the user or patient.

Figure 6:
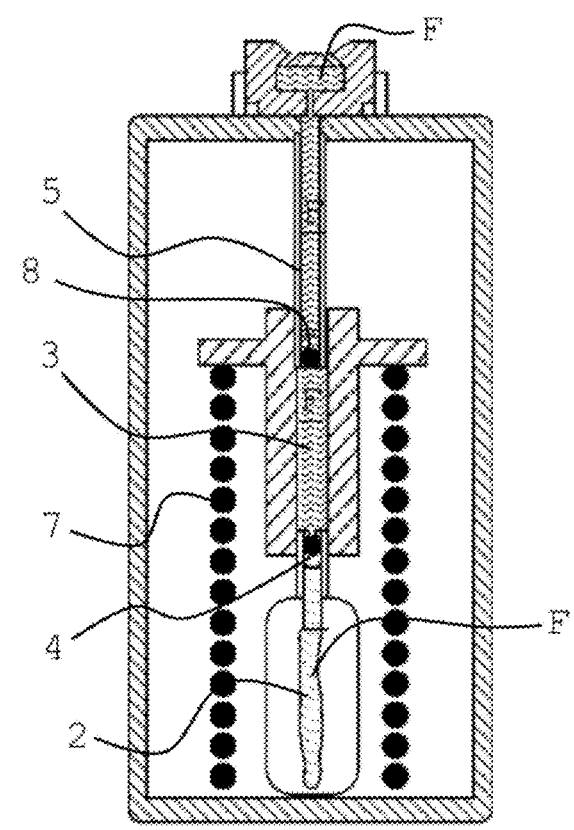
FIG. 6 shows the situation after re-filling the pumping chamber.

In FIG. 6, the inhalation device of FIG. 1 in the situation after re-filling the pumping chamber is depicted. The hollow cylinder (9) has been moved (repulsively) in an upstream direction, thus increasing the volume of the pumping chamber (3) provided by the cylinder (9). The means for the storage of potential energy (7) has been loaded (spring compressed). During movement of cylinder (9) away from the nozzle (6), a negative pressure has been generated in the pumping chamber (3), closing outlet valve (8) and opening the inlet check valve 4. As a result, further liquid (F) is drawn from reservoir (2) into the pumping chamber (3). The inhalation device's pumping chamber (3) is filled again and ready for the next election of liquid (F) by releasing the spring.

Figure 7:
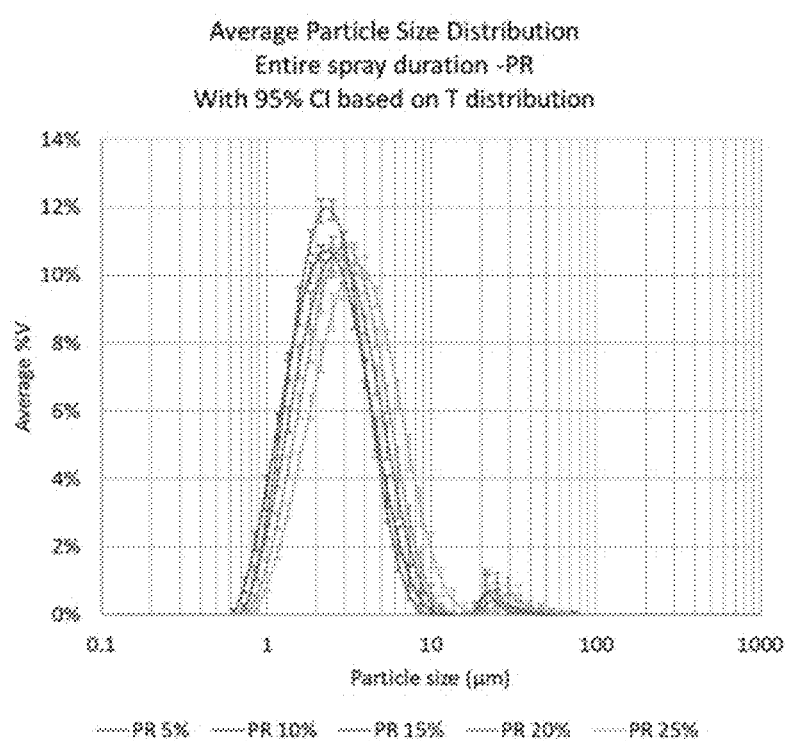
FIG. 7 shows the average particle size distribution results for Example 1.

FIG. 7 depicts the average particle size distribution for the entire spray duration of various combinations of water and ethylene glycol mixtures prepared to mimic the viscosity of a high molecular weight compound such as remdesivir at 5%, 10%, 15%, 20%, and 25% (wt. %) concentrations as described in Example 1. The particle size distribution is determined at a 95% confidence interval based on T distribution. The term "T distribution" also known as "Student's t-distribution" as used herein refers to a member of a family of continuous probability distributions that arises when estimating the mean of a normally distributed population in situations where the sample size is small and the population standard deviation is unknown.

Figure 8:
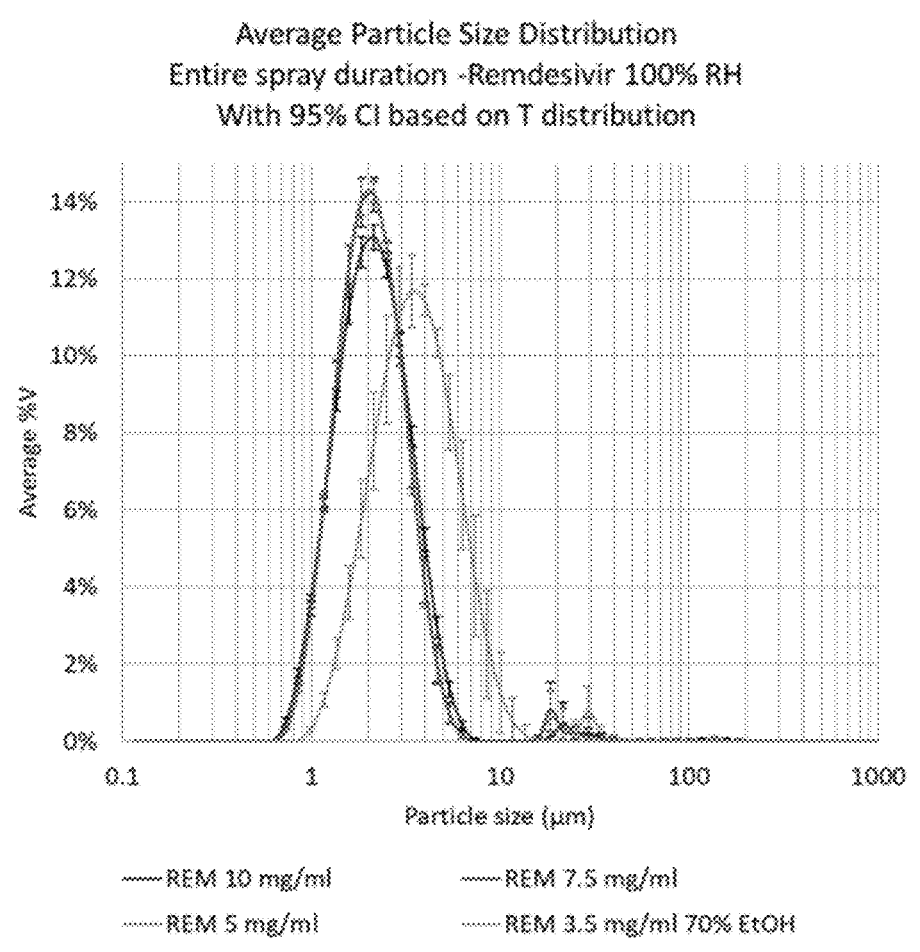

FIG. 8 depicts the average particle size distribution for the entire spray duration of various remdesivir concentrations (3.56, 5.08, 7.63, and 10.17 mg/ml) in 100% ethanol or 70:30 ethanol:water (% w/w) as described in Example 2. The particle size distribution is determined at a 95% confidence interval based on T distribution.

LIST OF REFERENCES

1 Housing
2 Fluid reservoir, reservoir
3 Pumping chamber
4 Inlet valve
5 Riser pipe
5A Interior end
5B Exterior end
6 Nozzle
7 Means for storing potential energy, means
8 Outlet valve
9 Hollow cylinder, cylinder
F Liquid, fluid, medically active liquid The following examples serve to illustrate the invention, however, should not be understood as restricting the scope of the invention.

EXAMPLES

Materials and Methods

For Example 1, solutions of water and ethylene glycol were prepared combining the two solvents at room temperature. For Example 2, solutions of remdesivir in ethanol (100%) were prepared by dissolving remdesivir in ethanol at room temperature. For Example 2, a solution of remdesivir in ethanol:water (70:30% w/w) was prepared by dissolving remdesivir in ethanol at room temperature and adding water to the solution. Each solution was dispensed using an embodiment of a soft mist inhaler as disclosed herein. Particle size distributions of the dispensed solutions were measured using a Malvern Spraytec® instrument.

Example 1

Solutions of water and ethylene glycol were prepared to mimic the viscosity of a high molecular weight compound such as remdesivir at concentrations of 5%, 10%, 15%, 20%, and 25% (wt. % of compound in solution). The wt/wt % values of ethylene glycol and water in each solution are summarized in Table 1.

TABLE 1

| Sample | Dynamic Viscosity | Relative Density | Water/Ethylene Glycol ratio (% w/w) |
| --- | --- | --- | --- |
| PR 5% | 1.66 | 0.8174 | 90% H$_2$O/10% EG |
| PR 10% | 1.93 | 0.8269 | 80% H$_2$O/20% EG |
| PR 15% | 2.15 | 0.8364 | 75% H$_2$O/25% EG |
| PR 20% | 2.47 | 0.8458 | 73% H$_2$O/27% EG |
| PR 25% | 2.91 | 0.8551 | 70% H$_2$O/30% EG |

Solutions were dispensed using an embodiment of a soft mist inhaler as disclosed herein at room temperature. The dispensing parameters and particle size distribution results are summarized in Table 2 and FIG. 7. The term "event duration" refers to entire spray duration in seconds (s) when the solution is dispensed.

TABLE 2

| Parameters | PR 5% | | PR 10% | | PR 15% | | PR 20% | | PR 25% | |
|---|---|---|---|---|---|---|---|---|---|---|
| | Mean (n = 6) | Stdev | Mean (n = 6) | Stdev | Mean (n = 6) | Stdev | Mean (n = 6) | Stdev | Mean (n = 6) | Stdev |
| Event duration/s | 2.34 | 0.15 | 3.95 | 0.00 | 3.95 | 0.00 | 3.96 | 0.00 | 3.96 | 0.01 |
| Dv10/μm | 1.19 | 0.02 | 1.10 | 0.03 | 1.24 | 0.02 | 1.40 | 0.03 | 1.57 | 0.03 |
| Dv50/μm | 2.20 | 0.05 | 2.10 | 0.07 | 2.49 | 0.10 | 2.78 | 0.09 | 3.26 | 0.12 |
| Dv90/μm | 4.22 | 0.17 | 4.48 | 0.16 | 5.14 | 0.34 | 5.67 | 0.29 | 6.87 | 0.52 |

Example 2

Solutions of remdesivir in ethanol (100%) and ethanol:water (70:30% w/w) were prepared at concentrations of approximately 3.56, 5.08, 7.63, and 10.17 mg ml. Solutions were dispensed using an embodiment of a soft mist inhaler as disclosed herein at room temperature. The dispensing parameters and particle size distribution results are summarized in Table 3 and FIG. 8. Addition of water increases the particle size.

TABLE 3

| Formulation | Spray duration (s) | Dv10 (μm) | Dv50 (μm) | Dv90 (μm) | Span | Ethanol content |
|---|---|---|---|---|---|---|
| REM 10.17 | 1.95 | 1.11 | 1.96 | 3.54 | 1.24 | 100% |
| REM 7.63 | 1.70 | 1.14 | 1.92 | 3.31 | 1.14 | 100% |
| REM 5.08 | 1.72 | 1.13 | 1.9 | 3.26 | 1.12 | 100% |
| REM 3.56 | 2.53 | 1.71 | 3.29 | 6.27 | 1.38 | 70% |

The invention claimed is:

1. A method for the treatment of a viral infection or viral disease, disorder or condition in a subject, the method comprising the step of administering to said subject 1 μL to 50 μL of a medically active liquid in nebulized form by inhalation,
wherein the medically active liquid comprises a therapeutically effective amount of remdesivir or a pharmaceutically acceptable salt thereof, wherein the medically active liquid is administered in nebulized form using an inhalation device, and wherein the inhalation device is a soft-mist-inhaler.

2. The method according to claim 1, wherein the viral infection or viral disease, disorder or condition is a coronavirus infection or a coronavirus disease, disorder or condition.

3. The method according to claim 2, wherein the coronavirus infection is a SARS-CoV or SARS-CoV-2 infection or the coronavirus disease, disorder or condition results from a SARS-CoV or SARS-CoV-2 infection.

4. The method according to claim 2, wherein the coronavirus infection is a Middle East respiratory syndrome coronavirus infection or the coronavirus disease, disorder or condition results from a Middle East respiratory syndrome coronavirus infection.

5. The method according to claim 1, wherein the viral infection or viral disease, disorder or condition is one which is responsive to inhibition of viral replication.

6. The method according to claim 1, wherein the viral disease, disorder or condition is a disease, disorder or condition of the immune system; an inflammatory disease, disorder or condition; an autoimmune disease, disorder or condition; a disease, disorder or condition of the cardiovascular system; a cancer; a tumor or other malignancy; a disease, disorder or condition of the renal system; a disease, disorder or condition of the gastro-intestinal tract; a disease, disorder or condition of the respiratory system; a disease, disorder or condition of the endocrine system; and/or a disease, disorder or condition of the central nervous system (CNS).

7. The method according to claim 1, wherein the viral disease, disorder or condition is an inflammatory disease, disorder or condition.

8. The method according to claim 1, wherein the viral disease, disorder or condition is a severe acute respiratory syndrome (SARS).

9. The method according to claim 1, wherein the viral infection or viral disease, disorder or condition is a respiratory or pulmonary infection or respiratory or pulmonary disease, disorder or condition.

10. The method according to claim 9, wherein the pulmonary infection is a lower respiratory tract infection.

11. The method according to claim 10, wherein the lower respiratory tract infection is a pneumonia.

12. The method according to claim 1, wherein the subject is a human or animal.

13. The method according to claim 1, wherein the subject is diagnosed with a viral infection or viral disease, disorder or condition.

14. The method according to claim 13, wherein the subject is diagnosed with COVID-19.

15. The method according to claim 1, wherein the remdesivir or pharmaceutically acceptable salt thereof is administered to the lungs of the subject.

16. The method according to claim 1, wherein the inhalation device used to administer the medically active liquid comprising remdesivir or a pharmaceutically acceptable salt thereof is a hand-held device.

17. The method according to claim 1, wherein the inhalation device used to administer the medically active liquid comprising the remdesivir or a pharmaceutically acceptable salt thereof is a soft-mist-inhaler having at least one impingement nozzle.

18. The method according to claim 1, wherein the inhalation device used to administer the medically active liquid comprising remdesivir or a pharmaceutically acceptable salt thereof is a hand-held inhalation device for delivering a nebulised medically active aerosol for inhalation therapy, comprising
(a) a housing having a user-facing side;
(b) an impingement nozzle for generating the nebulised aerosol by collision of at least two liquid jets, the nozzle being firmly affixed to the user-facing side of the housing such as to be immobile relative to the housing;
(c) a fluid reservoir arranged within the housing; and
(d) a pumping unit arranged within the housing, the pumping unit having
an upstream end that is fluidically connected to the fluid reservoir;

a downstream end that is fluidically connected to the nozzle;

wherein the pumping unit is adapted for pumping fluid from the fluid reservoir to the nozzle;

wherein the pumping unit further comprises
- (i) a riser pipe having an upstream end, wherein the riser pipe is
    adapted to function as a piston in the pumping unit, and
    firmly affixed to the user-facing side of the housing such as to be immobile relative to the housing; and
- (ii) a hollow cylinder located upstream of the riser pipe, wherein the upstream end of the riser pipe is inserted in the cylinder such that the cylinder is longitudinally movable on the riser pipe;
- (iii) a lockable means for storing potential energy when locked and for releasing the stored energy when unlocked, the means being arranged outside of, and mechanically coupled to, the cylinder such that unlocking the means results in a propulsive longitudinal movement of the cylinder towards the downstream end of the pumping unit.

19. The method according to claim 1, wherein the medically active liquid comprises a concentration of remdesivir of about 10 µg/µL to about 30 µg/µL.

20. The method according to claim 1, wherein the viral infection or viral disease, disorder or condition is severe acute respiratory syndrome coronavirus (SARS-CoV), Middle East respiratory syndrome coronavirus (MERS-CoV), Ebola virus (EBOV), Marburg virus, respiratory syncytial virus (RSV), Nipah virus (NiV), and Hendra virus.

\* \* \* \* \*